(12) United States Patent
Hairrell (10) Patent No.: US 9,364,301 B2
(45) Date of Patent: Jun. 14, 2016

(54) DENTAL WAX APPLICATOR

(71) Applicant: Loyd G. Hairrell, Denton, TX (US)

(72) Inventor: Loyd G. Hairrell, Denton, TX (US)

(*) Notice: Subject to any disclaimer, the term of this patent is extended or adjusted under 35 U.S.C. 154(b) by 437 days.

(21) Appl. No.: 13/952,702

(22) Filed: Jul. 29, 2013

(65) Prior Publication Data
US 2015/0030992 A1 Jan. 29, 2015

(51) Int. Cl.
*A61C 3/00* (2006.01)
*A61C 13/00* (2006.01)

(52) U.S. Cl.
CPC .................. *A61C 13/0028* (2013.01)

(58) Field of Classification Search
CPC ...... A61C 1/02; A61C 13/0001; A61C 13/00; A61C 13/20; A61C 19/004; H05B 6/06; H05B 3/40
USPC ............ 219/241, 229, 254, 259; 433/27, 213, 433/32
See application file for complete search history.

(56) References Cited

U.S. PATENT DOCUMENTS

| | | | | | |
|---|---|---|---|---|---|
| 3,614,389 | A * | 10/1971 | Malisza | ............ | A61C 13/0028 126/343.5 A |
| 3,831,815 | A * | 8/1974 | Glasgow | ............ | A61C 13/0028 219/230 |
| 3,902,043 | A * | 8/1975 | Rogan | .................... | A61C 13/20 219/230 |
| 4,802,846 | A * | 2/1989 | Posca | ................. | A61C 13/0028 433/32 |
| 5,061,178 | A * | 10/1991 | Ueno | ................. | A61C 13/0028 222/146.5 |
| 6,441,345 | B1 * | 8/2002 | Usui | .................. | A61C 13/0028 219/227 |
| 6,524,102 | B2 * | 2/2003 | Davis | .................. | A61C 9/0006 222/146.5 |
| 7,175,429 | B2 * | 2/2007 | Guidi | ...................... | H05B 3/46 219/229 |
| 2014/0054319 | A1 * | 2/2014 | Shin | ....................... | B65D 83/14 222/146.5 |

* cited by examiner

*Primary Examiner* — Nina Bhat
(74) *Attorney, Agent, or Firm* — Jeffrey Roddy

(57) ABSTRACT

A system enabling precise control of dental wax application by fine temperature control includes a PID thermostatic controller, at least one cartridge heater and a temperature sensor. The cartridge heaters are embedded in a heater block containing heating that transfers heat to a barrel of a wax applicator when the barrel is intermittently placed into a heating chamber of the block.

4 Claims, 7 Drawing Sheets

FIG.9a

DENTAL WAX APPLICATOR

FIELD

The present invention relates generally to an apparatus for extruding dental wax used for dental lab applications.

BACKGROUND

Dental wax extruders of various design have been described in the past. Typically such devices are in the form of a gun or extruder, similar in some ways to a hot glue gun and possessing a heating element to heat the wax which is advanced manually, or by other means, in order to extrude wax for use in molds, dental prosthesis and other applications.

U.S. Pat. No. 3,831,815 to Glasgow discloses a dental wax extruder that uses hydraulic fluid to heat and pressurize a collapsible pre-packaged cartridge of dental wax whereby the wax is extruded from a nozzle.

U.S. Pat. No. 6,524,102 to Davis discloses a thermoplastic extruder for applying border molding to denture impression trays and includes thermoplastic sticks which are inserted into a dispenser with a heating element. The thermoplastic sticks are manually forced through a heated portion of the extruder which has heat exchange surfaces that can be shielded by a user's hand to control heat loss.

While the foregoing devices offer advantages for their intended use, problems persist for the dental lab practitioner and clinician. One issue is cording or tubing which tether the extruders to a power source that get in the way of the wax application process and negatively impact the quality of the work being performed. Another issue is wax degradation or unpredictable altering of its intended or recorded rheological properties. Although recent formulations of dental wax offer advantages with regard to workability at elevated temperature, the melting range tends to be more narrow than in the past. Zhang, Kehao "Rheological characterization of dental waxes" Eberhard Karls University, Tübingen 2004. Of particular concern is material degradation resulting from imprecise heating and fluctuating temperatures which can adversely affect wax properties to the extent that the wax must be discarded.

It would be desirable to provide a dental wax application system that includes a wax applicator, is relatively lightweight, untethered and easy to manipulate.

It would be further desirable if the foregoing system include a means to program and precisely regulate wax temperature within a range of +0.5 to −0.5 C for a selected wax in order to provide a regular flow of softened wax that can be maintained for extended periods at a selected temperature range in order to improve work readiness, optimize wax working properties and extend the life of the wax.

SUMMARY

The present invention is a dental wax application system for both lab and clinical use that includes a heating unit with a heater block of sufficient mass made of a thermally conductive material such as aluminum and heated by means of cartridge heaters which are controlled by a proportional integral and derivative (PID) controller capable of maintaining the heater block at a range of a range of +0.5 to −0.5 C, that will permit a user to program and store a set of selectable temperature ranges for various waxes. PID control permits more stable temperature range management than other types of temperature control such as on/off control, or proportional control. Suitable PID controllers for the invention include, but are not limited to auto-tune type controllers such as the EZ-ZONE PM Temperature Controller Series from Watlow Inc. 12001 Lackland Rd. St. Louis, Mo. USA 63146, that provide for adaptive temperature sensing and learning, whereby the controller initially probes a material to determine its thermal properties which are then employed in the controller's PID algorithm. According to a preferred embodiment described herein, a hand held wax applicator for use with the heater block includes a body with a barrel, handle and trigger that when pulled, moves a piston forward within the barrel for extruding a portion of wax contained therein. The detachable barrel which is made of a conductive material such as aluminum possesses a coupling means at one end and a nozzle at the other end. While the barrel and nozzle of the embodiment depicted herein are one piece construction, interchangeable nozzles of various shapes and sizes can be used without departing from the scope of the invention. When the applicator is not being held, the barrel is inserted in one of the cylindrical chambers formed in the heater block whereby heat is transferred from the block to the wax by convection initially, and then convection/conduction. While the working time for a wax loaded applicator once removed from the chamber varies with the type of wax, it is generally from 1 to 2 minutes. For example, the working time of set-up wax which is used to set teeth in dental prosthesis, and has a broad flow range, is approximately 1.5 minutes, whereas, re-softening by reinserting the barrel in the heating chamber takes approximately 1 minute. Preferably, a technician would set the temperature for set-up wax based on ambient temperature. In the particular embodiment depicted herein, the heating means for the heater block are cartridge heaters fitted into apertures adjacent each chamber in the heater block so that the bore of the chambers and apertures are parallel. A temperature sensor such as a thermocouple or resistance temperature detector (RTD) is inserted in an additional aperture in the heater block, and provides block temperature feedback for the PID controller which is displayed on the PID as the "process value."

Types and Properties of Dental Wax

Dental waxes are of various composition with so called mineral waxes being the most commonly employed in the dental lab. Properties of strength, proportional limit and elastic modulus of wax decreases at higher temperatures. Waxes possess a melting range, not a melting point, and flow increases near the melting range. Uniform heating of wax before its use in dental lab applications reduces thermal distortion.

Paraffin is one of the more frequently used mineral waxes. Unmodified paraffin when cooled, contracts non-uniformly in volume 11-15% due to numerous phase transitions. Microcrystalline wax, another mineral wax, has a greater molecular weight than paraffin, is more flexible, contracts less upon cooling than paraffin, and can be added to a paraffin base with or without mineral additives such as Barnsdahlm, Ozokerite or Ceresin in order to modify properties such as widening the melting range or raising melting range. The wide range of waxes that are proprietary formulations and those custom mixed at the lab mean there are many melting temperature ranges, and within the melting ranges a subset of optimal temperatures depending on the specific application.

In one aspect of the present invention, an untethered dental wax applicator possesses a removable barrel that maintains wax contained therein at a desired temperature in order to provide extended working times and prevent premature degradation of the wax resulting from excessive temperature fluctuations or wide swings in temperature.

In another aspect of the present invention, a heating unit comprises a heater block that serves to transfer heat to an applicator, and allows a user to pre-program a set of selectable temperature ranges depending on the wax used.

The foregoing and other objects, features, and advantages of the invention will become more apparent from the following detailed description, which proceeds with reference to the accompanying figures wherein the scale depicted is approximate.

DETAILED DESCRIPTION OF THE INVENTION

Reference Listing 100 wax system
200 applicator
210 plunger shaft
212 coupler
220 barrel
230 piston
235 trigger grip
240 outlet/nozzle
245 threaded coupling
300 heater assembly
305 faceplate
306 faceplate aperture
310 chamber
320 heater block
325 heating block aperture
330 cartridge heater
340 temperature sensor
360 thermostat/regulator
370 relay

DEFINITIONS

In the following description, the term "heater block" refers to a heat reservoir of a material with thermal properties discoverable by, and regulated by PID control. The term "coupling means" can mean any means for removably connecting the wax barrel to the applicator, whether threaded connection or other connection which would be appreciated by those skilled in the art with benefit of this disclosure. The term "thermostatic heat control" or "thermostatic controller" means a PID controller or a thermo-controller of equal or better resolution/range control. Unless otherwise explained, any technical terms used herein have the same meaning as commonly understood by one of ordinary skill in the art to which this disclosure belongs. The singular terms "a", "an", and "the" include plural referents unless the context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

Referring generally to FIGS. 1 through 9b, a system for a dental wax application includes a applicator 100 having a detachable barrel 220 that is filled with a charge of a wax with rheological properties selected for a particular application. The applicator has a body with an internal friction action (not shown) whereby plunger shaft 210 and piston 230 are driven forward within the barrel when trigger grip 235 is pressed in order to extrude a desired amount of softened wax from outlet 240. The barrel is made of a thermally conductive material such as aluminum and is preferably of machined, cast or sintered construction. The system includes a heater block 320 which like the barrel, is also made of a thermally conductive material such as aluminum. The heater block preferably includes a number of apertures that define chambers 310 for the insertion of the barrel end of the applicator whereby heat from the heater block is transferred by convention and conduction to the wax a user has placed in the barrel. A series of cartridge heaters 330 are embedded in the heater block, typically inserted into machined apertures 331 having a coating of thermal grease for a close fit. Apertures housing the cartridge heaters are adjacent chambers 310. An additional aperture 341 houses a temperature sensor 340, typically either a thermocouple or RTD for temperature sensing of the block and feedback to a PID thermostatic controller 360 which maintains the heater block at a temperature range that can be a narrow range of +0.5 to −0.5 C or greater as desired and selected by the user. Conductive heat transfer from the block to the barrel of the applicator insures (1) a steady rise in temperature without spiking to the desired range, and avoids temperature overshoot which would alter the wax working properties, and (2) insures that the wax manufacturers specified optimal temperature range is maintained to prevent premature wax degradation of sensitive waxes.

Figures 1, 2, 3:
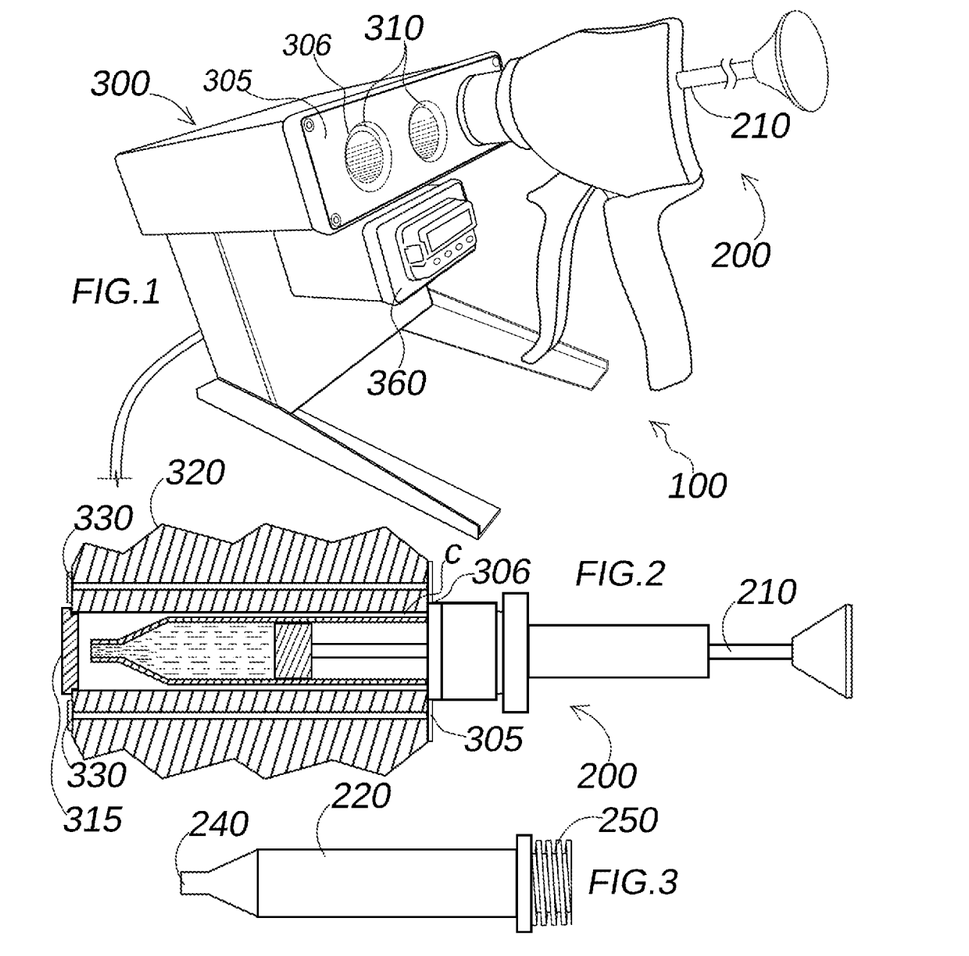
FIG. 1 is a perspective view showing the heating assembly and applicator according to the present invention.
FIG. 2 is a partial cutaway view of a heater block 320 with inserted barrel according to one embodiment of the present invention.
FIG. 3 is a side plan view of barrel 220 according to one embodiment of the present invention.

FIG. 1 shows chambered 310 heating block 320 with barreled 220 end of applicator 200 inserted therein. Preferably, the material of the heating block bore and the material of the extruder barrel are the same. Clearance (c), between the barrel and the chamber, while exaggerated in (FIG. 2), is preferably between 0.001 and 0.008 inch, and even more preferably between 0.001 and 0.003 inch, which is critical to heat transfer from the heating block to the barrel by minimizing air space between the barrel and the heating block bore, thus providing efficient thermoconvective transfer to the barrel and subsequent thermoconvective and thermoconductive transfer to the wax. Relatively small clearances also mean that the temperature of the heater block and the barrel provide for more accurate temperature readings by the PID controller. The PID controller provides a means to auto-tune for its intended use. For example, the tuning process is initiated the first time the controller is powered up in order for it to "learn" the properties of the material to be heated. The PID intermittently heats and polls time/temperature and ceases heating and polls time/temperature, allowing the material to cool. In this way, the thermal properties of the material such as heat gain and loss are recorded for use in the subsequent PID algorithm. When maintaining a selected range, the controller compares the instant time/temperature to that of previous time/temperatures to predict a future instant time/temperature so that it can determine the instant time to reduce current to the cartridge heaters and thus avoid temperature overshoot or undershoot.

FIG. 2 is a partial cutaway of a chambered portion of the heater block 320 and inserted applicator 200 barrel 220 with plunger shaft 210 and piston 230. Cartridge heaters 330 are shown embedded on either side of chamber 310. A removable cap 315 seals the chambers at the back side of the heater block. While preferably, the heater block and the barrel of the described embodiment is formed from 6000 series aluminum, although other similarly thermoconductive materials can be used without departing from the scope of the invention.

FIG. 3 is a side plan view of barrel 220 having a outlet 240 and threaded coupling 245 at the respective ends. While in the embodiment shown, the barrel coupling is threaded, the particular coupling means can be any that would suggest itself to those having skill in the art and benefit of this disclosure.

Figure 4:
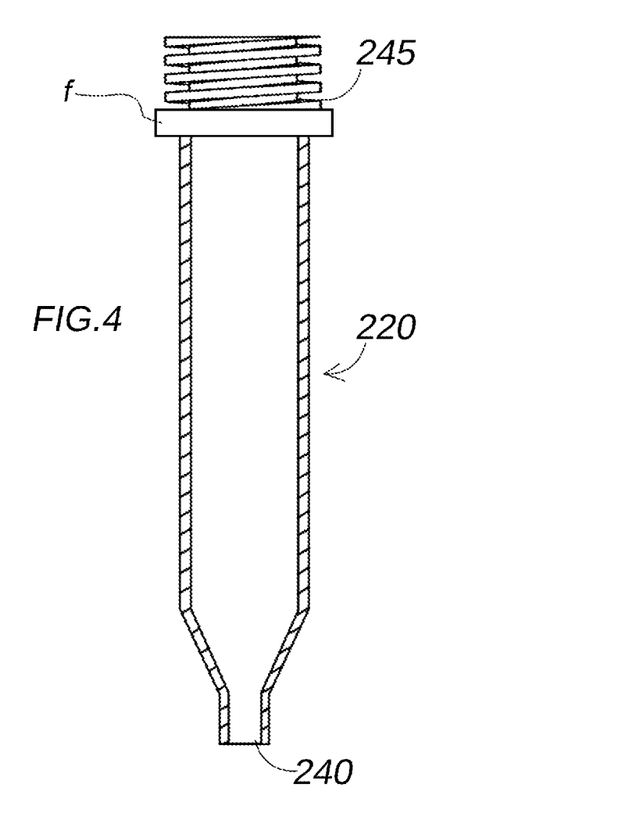
FIG. 4 is an enlarged partial cutaway view of the barrel of (FIG. 3)
Figure 5:
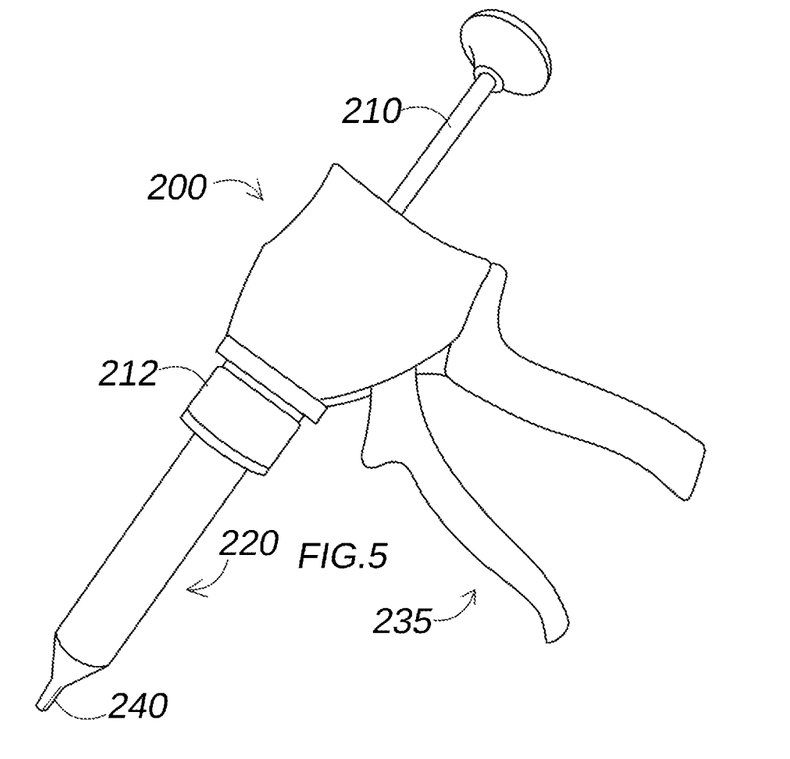
FIG. 5 is a side perspective view of assembled wax applicator 200.

FIG. 4 is an enlarged partial cutaway of the barrel of (FIG. 3) taken starting below the coupling showing the interior of the barrel.

Figure 6:
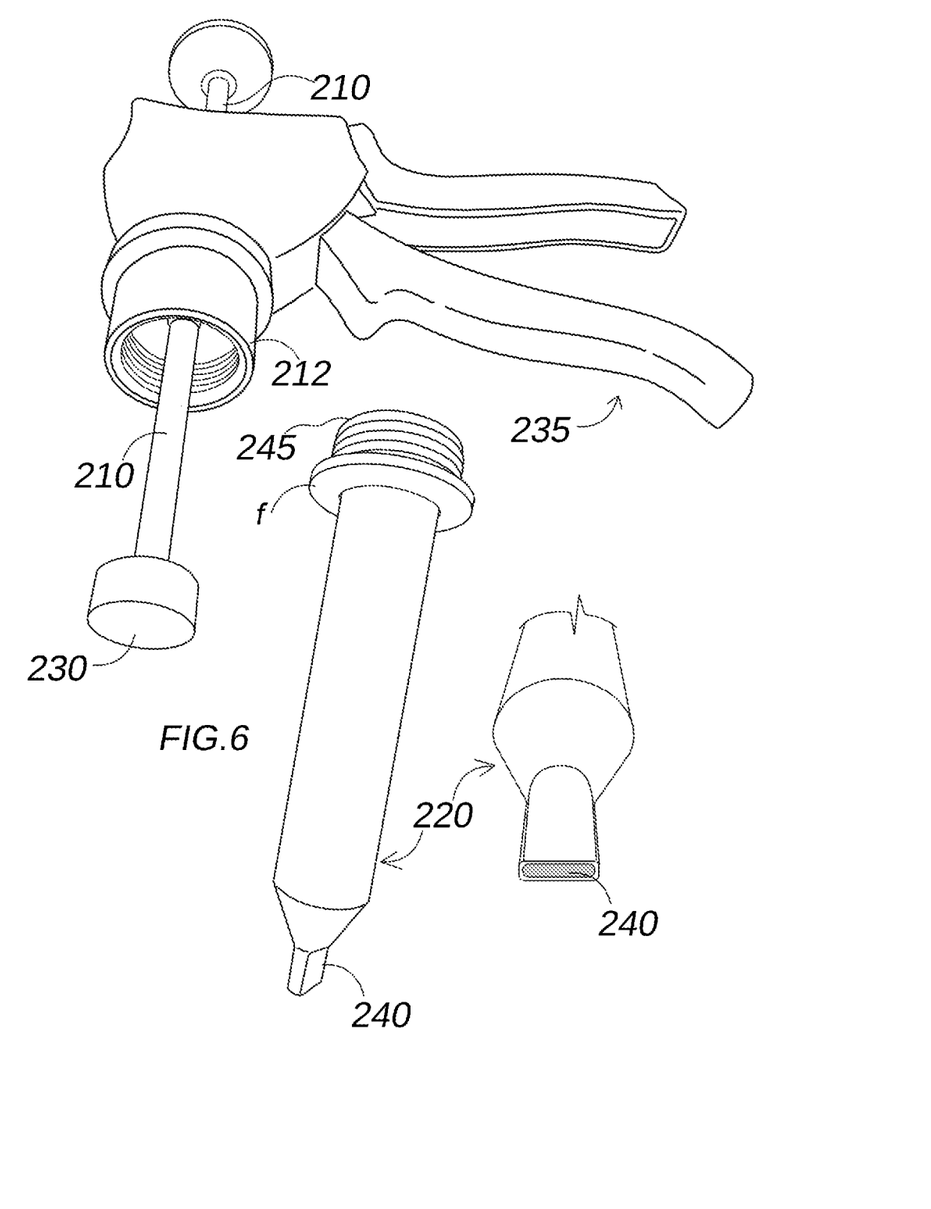
FIG. 6 is a perspective view showing wax applicator of (FIG. 5) with barrel 220 removed showing plunger shaft 210 and piston 230.

FIG. 6 s a perspective view showing the wax applicator 200 (FIG. 5) with barrel 220 removed showing coupler 212, barrel outlet 240, plunger shaft 210 and piston 230. While the wax applicator depicted possesses a common friction grip design whereby plunger shaft 210 is moved froward by intermittent gripping by a portion of the applicator when actuated by the trigger, it can be of any design capable of moving the shaft forward when the trigger is pulled. It should be noted that just below the threads on the barrel is a circular flange (f) that provides a seal to an end of a heating chamber when the barrel is inserted therein.

Figure 7:
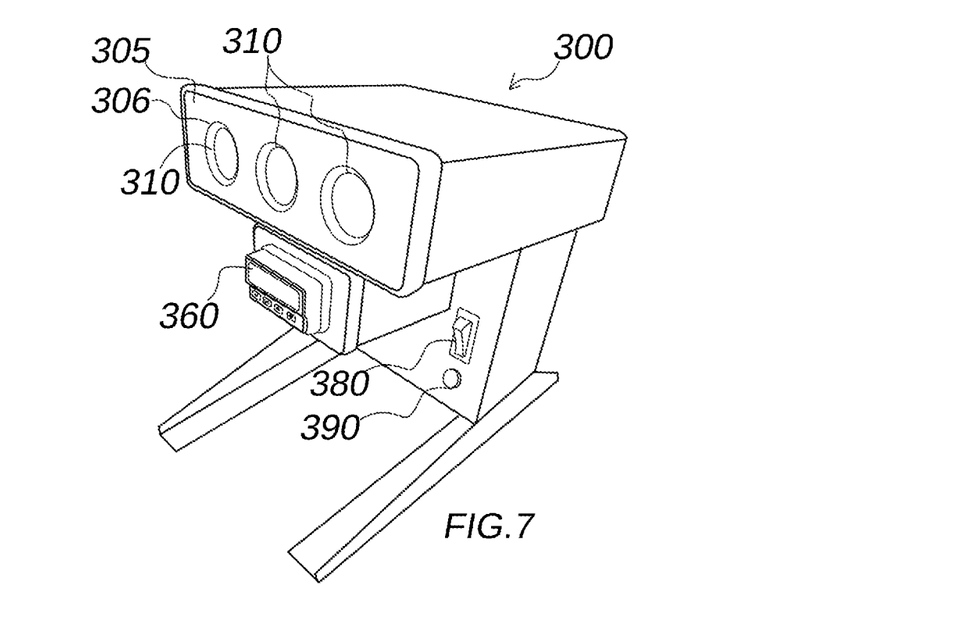
FIG. 7 is a perspective view of the exterior of a heating unit 300 according to one embodiment of the present invention.

FIG. 7 is an exterior perspective view of heating unit 300 with programmable heat controller 360, on/off switch 380 and readiness indicator light 390. When the barrel of the applicator is placed in one of the heating chambers, coupler 212 is abuts inside diameter of faceplate aperture 306 thereby centering the barrel within the chamber.

Figure 8:
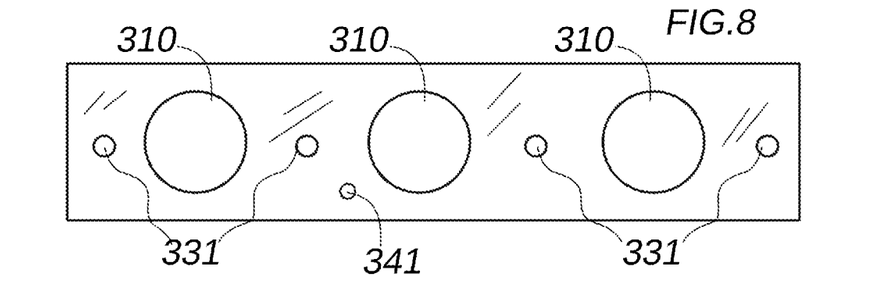
FIG. 8 is rear plan view of the heater block 320 showing relative positioning of heater cartridge apertures 331, chambers 310 and thermocouple aperture 341.

FIG. 8 is a rear plan view of the heater block 320 that shows the relative positions of heating chambers 310, cartridge heater apertures 331 and thermocouple aperture 341. While in the particular embodiment depicted possesses three heating chambers, which permits three applicators to be used, the heater block can have one or any number of heating chambers, at least one thermocouple or RTD, and at least one cartridge heater.

Figure 9A:
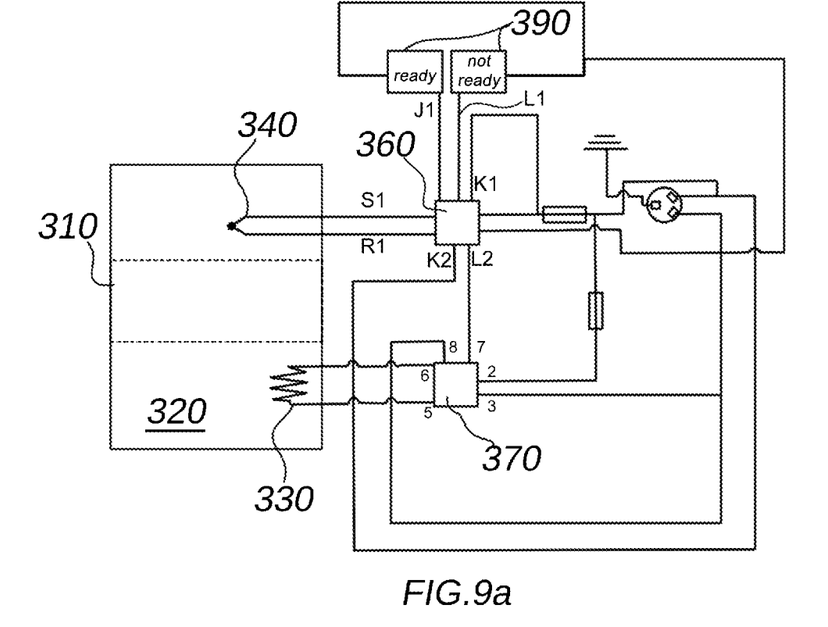
FIG. 9a is a circuit diagram of a preferred embodiment according to the present invention.
Figure 9B:
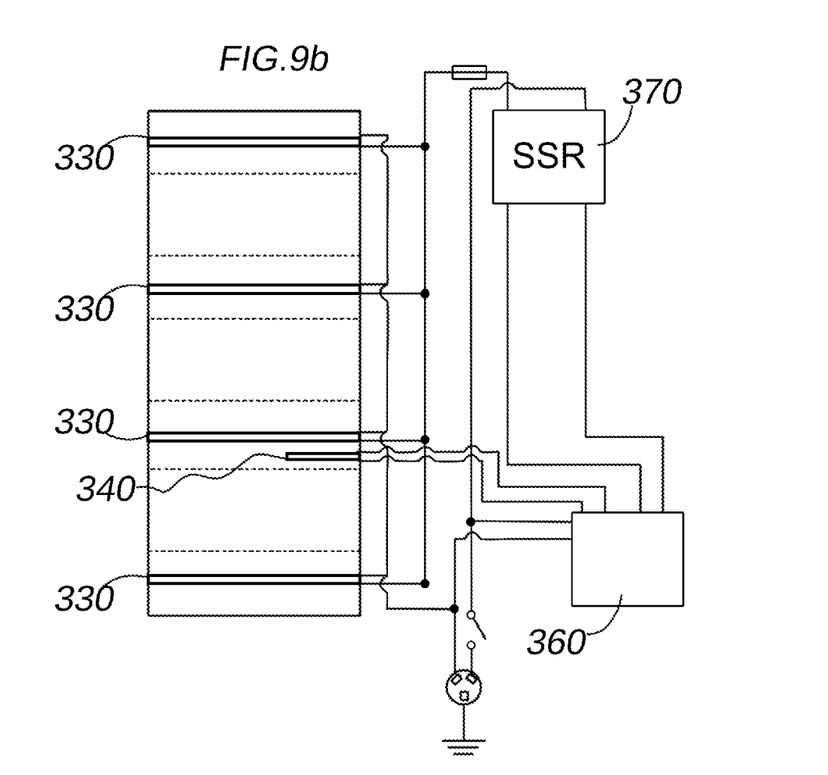
FIG. 9b is an alternate circuit diagram according to an embodiment of the present invention.

FIGS. 9a and 9b show typical circuit diagrams for use with a preferred embodiment, that include a PID controller 360, solid state relay 370, temperature sensor 340 and cartridge heaters 330. Persons having skill in the art and benefit of this disclosure will appreciate that the diagrams depicted are but two exemplary circuits, and this disclosure is intended to cover common alternates, modifications and substitutions to the circuitry.

It should be understood that the drawings and detailed description herein are to be regarded in an illustrative rather than a restrictive manner, and are not intended to be limiting to the particular forms and examples disclosed. For example, while the wax applicator disclosed herein makes use of a friction grip action to move the plunger shaft and piston forward in the barrel, as will be appreciated by those having skill in the art, ratcheting mechanisms of various design can be employed in the applicator to force the plunger shaft and piston without departing from the instant invention. Accordingly, it is intended that this disclosure encompass any further modifications, changes, rearrangements, substitutions, alternatives, design choices, and embodiments as would be appreciated by those of ordinary skill in the art having benefit of this disclosure, and falling within the spirit and scope of the following claims.

What is claimed is:

1. A dental wax application system for precise control of wax flow and for prolonging the useful life of wax comprising:
   a housing including:
      a programmable PID thermostatic controller capable of storing multiple temperature set points, and, at least one heater block having at least one heating chamber;
   at least one electrically untethered applicator for extrusion of wax comprising:
      a removable barrel with an outlet, a plunger shaft and a piston moveable longitudinally within the barrel, wherein the barrel and wax contained therein is maintained at a desired temperature by intermittent insertion into the at least one heating chamber, and wherein the piston is manually actuated.

2. The system according to claim 1, further comprising at least one cartridge heater and temperature sensor on or in the heater block and connected to the controller.

3. The system according to claim 1, in which the thermostatic controller is capable of maintaining a temperature range of +0.5° C. to −0.5° C. relative to a selected temperature set point.

4. The system according to claim 1 in which clearance between the heating chamber and the barrel when inserted therein is between 0.001 and 0.008 inch.

* * * * *